US010606062B2

United States Patent
Duckett, III et al.

(10) Patent No.: US 10,606,062 B2
(45) Date of Patent: Mar. 31, 2020

(54) MEDICAL IMAGING DEVICE WITH SPLIT IMAGE ON COMMON IMAGE SENSOR

(71) Applicant: KARL STORZ Imaging, Inc., Goleta, CA (US)

(72) Inventors: George E. Duckett, III, Castaic, CA (US); Marios Kyperountas, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 16/013,634

(22) Filed: Jun. 20, 2018

(65) Prior Publication Data
US 2019/0391383 A1    Dec. 26, 2019

(51) Int. Cl.
*A61B 1/06*        (2006.01)
*G02B 23/04*    (2006.01)
(Continued)

(52) U.S. Cl.
CPC .......... *G02B 23/04* (2013.01); *A61B 1/00186* (2013.01); *A61B 1/00188* (2013.01); *A61B 1/00197* (2013.01); *A61B 1/05* (2013.01); *A61B 1/055* (2013.01); *A61B 1/0676* (2013.01); *G02B 13/08* (2013.01); *G02B 23/2438* (2013.01); *G02B 27/1013* (2013.01); *G06T 5/007* (2013.01); *G06T 5/50* (2013.01);
(Continued)

(58) Field of Classification Search
CPC ............................. G02B 23/04; A61B 1/00186
See application file for complete search history.

(56) References Cited

U.S. PATENT DOCUMENTS 4,857,724 A    8/1989  Snoeren
5,216,512 A    6/1993  Bruijns
(Continued)

FOREIGN PATENT DOCUMENTS

| EP | 295728 A1 | 12/1988 |
|----|-----------|---------|
| EP | 469678 A1 | 2/1992 |
| JP | 2004313523 | 11/2004 |

OTHER PUBLICATIONS

Windecker, R., European Search Report; App 19000278.2-1020, Nov. 14, 2019, pp. 1-5, Munich.

*Primary Examiner* — Thai Q Tran
*Assistant Examiner* — Girumsew Wendmagegn
(74) *Attorney, Agent, or Firm* — Michael Joseph Loi; David Noel Villalpando (57) ABSTRACT

Medical imaging camera head devices and methods are provided using light captured by an endoscope system or other medical scope or borescope. Afocal light from the scope is manipulated and split. The resulting first and second beams are passed through focusing optics to a single sensor. To take better advantage of the available number image sensor pixels, the beam may pass through lens elements (or prisms) to generate an anamorphic aspect ratio prior to being split, increasing the resolution of the image in one dimension. The afocal anamorphic beam is then split, and both images are focused on the image sensor. The anamorphism is compensated for in image processing, permitting higher resolution in one dimension along the image sensor. The manipulation of the beams prior to being split (and in some cases after or while being split) can take several forms, each offering distinct advantages over existing systems.

26 Claims, 8 Drawing Sheets

(51) Int. Cl.
*H04N 5/265* (2006.01)
*H04N 5/33* (2006.01)
*G06T 5/00* (2006.01)
*G06T 5/50* (2006.01)
*H04N 5/232* (2006.01)
*G02B 23/24* (2006.01)
*G02B 13/08* (2006.01)
*G02B 27/10* (2006.01)
*A61B 1/00* (2006.01)
*A61B 1/05* (2006.01)
*A61B 1/055* (2006.01)
*H04N 5/225* (2006.01)

(52) U.S. Cl.
CPC ....... *H04N 5/2256* (2013.01); *H04N 5/23212* (2013.01); *H04N 5/23232* (2013.01); *H04N 5/265* (2013.01); *H04N 5/332* (2013.01); *G06T 2207/10048* (2013.01); *G06T 2207/10068* (2013.01); *G06T 2207/10152* (2013.01); *G06T 2207/20221* (2013.01); *H04N 2005/2255* (2013.01)

(56) References Cited

U.S. PATENT DOCUMENTS

| | | | |
|---|---|---|---|
| 5,689,365 | A | 11/1997 | Takahashi |
| 6,659,940 | B2 | 12/2003 | Adler |
| 8,675,043 | B2 | 3/2014 | Duparre |
| 8,784,301 | B2 | 7/2014 | McDowall |
| 8,988,539 | B1 | 3/2015 | Pascoguin |
| 8,994,802 | B2 | 3/2015 | Suga |
| 9,510,739 | B2 | 12/2016 | Adler |
| 2002/0035330 | A1* | 3/2002 | Cline ................ A61B 1/00009 600/476 |
| 2002/0057496 | A1 | 5/2002 | Kanai |
| 2005/0200847 | A1 | 9/2005 | Chen |
| 2006/0171021 | A1* | 8/2006 | Scott ......................... G01J 9/00 359/362 |
| 2013/0038689 | A1 | 2/2013 | McDowell |
| 2013/0041226 | A1 | 2/2013 | McDowell |
| 2013/0235174 | A1 | 9/2013 | Namii |
| 2017/0351103 | A1 | 12/2017 | Duckett |

* cited by examiner

MEDICAL IMAGING DEVICE WITH SPLIT IMAGE ON COMMON IMAGE SENSOR

TECHNICAL FIELD OF THE INVENTION

The invention relates generally to the field of medical image capture and more specifically to endoscopic camera designs with improved dual imaging.

BACKGROUND OF THE INVENTION

Dual image acquisition can be a useful feature in the field of endoscopy. Two video streams of the same scene are captured, but each of the captured image streams has different associated characteristics such as a variation in light spectrum, depth of field, or light intensity. In prior dual image systems, images have generally been collected, split in image space, and then focused onto two independent detectors. Such a configuration allows for more versatility than a single image acquisition system, but is generally more expensive and complex, requiring at least two sensors and associated electronics and mounting assemblies.

Some prior art systems do capture multiple images from a single chip, however they generally contain a beamsplitter in the image space of the camera. Such designs have significant limitations due to lack of flexibility in positioning desired optical elements such as filters, lenses, and other elements in the optical paths after the beam is split. Further, the cost of a dual image system may be higher due to the duplication of certain optical components used in focusing and detecting the image light of the dual channels.

What is needed are devices and methods to enable an endoscopic camera to acquire dual images in a cost effective manner. What is further needed are devices allowing the use of varied existing endoscopes for dual imaging applications, and allowing the detection of the varied characteristics in the dual images.

SUMMARY OF THE INVENTION

It is an object of the invention to provide improved endoscope acquisition of dual images, and to allow the use of varied existing endoscopes for dual imaging applications. It is another object to make the most effective use of high definition image sensors in dual imaging applications. It is a further object of the invention to allow detection of varied characteristics in the dual images, based on ability to vary the characteristics of the optical channels of the dual images.

Endoscopic camera head devices and methods are provided using light captured by an endoscope system. Substantially afocal light from the endoscope is manipulated and split by a beamsplitter. The resulting first and second beams are passed through focusing optics to fall on a single sensor. In order to take better advantage of the available number image sensor pixels, the beam may pass through cylindrical lens elements (or prisms) to generate an anamorphic aspect ratio prior to being split, increasing the resolution of the image in one dimension. The afocal, anamorphic beam is then split, and both images are focused on the image sensor. The anamorphism is compensated for in image processing, permitting higher resolution in one dimension along the image sensor. The manipulation of the beams prior to being split (and in some cases after or while being split) can take several forms, each offering distinct advantages over existing systems.

According to a first aspect of the invention, an optical imaging system for use with a medical scope is provided, including a first optical group with a beamsplitter optically arranged to receive single optical image light in an afocal state and split the single optical image into a first portion of light directed along a first optical path and a second portion of light directed along a second optical path. A second optical group includes refractive elements optically arranged to receive the first and second portions of light from the beamsplitter and focus the first portion as a first image onto a first area of a common image sensor and focus the second portion as a second image onto a second area the common image sensor wherein the first and second image areas of the common sensor do not overlap. One or more manipulating optical means are located upstream of the second optical group to manipulate one or more of the single optical image light, the first portion of light and the second portion of light.

According to some implementations of the first aspect, one or more of the manipulating optical means is an element of the first optical group. The one or more of the manipulating optical means may include an anamorphic optical element in the first optical group, optically arranged to receive the single optical image light in an afocal state such that the resulting images have an anamorphic aspect ratio. The manipulating optical means may be the beamsplitter. The anamorphic optical elements may be prisms constructed to induce the anamorphic aspect ratio, or may be lenses constructed to induce the anamorphic aspect ratio.

According to some implementations of the first aspect, the one or more manipulating optical means include a spectral filter whereby the spectral content of the first portion of light differs substantially from the spectral content of the second portion of light. The first portion of light may include infrared content, with the second portion of light including visible light. The system may include an image processor programmed to process the first and second images to generate a single combined image with the two different spectral contents overlaid.

According to some implementations of the first aspect, the one or more manipulating optical means includes a means to manipulate the light intensity of the first portion of light such that it has a different intensity than the second portion of light. The system may include an image processor programmed to process the first and second images to generate a single combined image with higher dynamic range than either the first or second image taken individually.

According to some implementations of the first aspect, the one or more manipulating optical means includes an optical element in the first optical path that is not present in the second optical path such that the first image is brought to a different focus on the common image sensor. The system may include an image processor programmed to process the first and second image to generate a single image with an enhanced depth of field over either the first or second image taken individually.

According to some implementations of the first aspect, the one or more manipulating optical means include a magnification means to manipulate the first portion of light such that the first and second image have a different magnification at the image sensor. According to some implementations of this aspect, the single optical image light is split unequally by intensity such that the majority of divided intensity is dedicated to the magnified beam in order to compensate for a lower intensity collected in the field of view of the magnified image. The image splitting inequality may be specifically selected such that the resulting first and second image have substantially equal intensities.

According to a second aspect of the invention, a method is provided for producing enhanced images from a medical scope. The method includes collecting image light from an illuminated scene. The method then directs the image light from the medical scope along a single optical channel with the image light in a substantially afocal state, and splits the image light from the single optical channel into a first portion of light and a second portion of light. The method optically manipulates one or more of the image light directed along a single optical channel, the first portion of light, and the second portion of light. The method directs the first portion of light along a first optical path and the second portion of light along a second optical path, and focuses the first portion of image light on a first area of an image sensor and forms a first detected image. The method focuses the second portion of image light on a second portion of the image sensor, separate from the first area of the image sensor, and forms a second detected image. The method then processes image data from the first and second portions of the image sensor.

According to some implementations of the second aspect, the method generates a single combined image by combining elements of the first detected image and elements of the second detected image.

According to some implementations of the second aspect, the step of optically manipulating one or more portions of light includes manipulating the image light in the single optical channel to have an anamorphic aspect ratio.

According to some implementations of the second aspect, the step of optically manipulating one or more portions of light includes filtering the spectral content of the first portion of light such that it differs substantially from the spectral content of the second portion of light. Filtering the first portion of light may include filtering wavelengths outside of the infrared spectrum such that the content of the first portion of light includes infrared light and the second portion of light includes visible light.

According to some implementations of the second aspect, the step of optically manipulating one or more portions of light includes attenuating the first portion of light such that it has a different intensity than the second portion. The step of processing the image data may also include generating a single combined image with higher dynamic range than either the first or second detected image taken individually.

According to some implementations of the second aspect, the step of optically manipulating one or more portions of light includes focusing the first image on the common image sensor differently than focusing the second image on the common image sensor, and the image processing step includes generating a single image with an enhanced depth of field over that of either the first or second detected images taken individually.

According to a third aspect of the invention, an optical device for use in endoscope procedures is provided, including a first optical group with one or more anamorphic optical elements optically arranged to receive light of a single optical image, and a beamsplitter optically arranged to receive the single optical image light from the one or more anamorphic optical elements in an afocal state and split the single optical image into a first portion of light directed to a first optical path and a second portion of light directed to a second optical path. A second optical group including refractive elements is optically arranged to receive the first and second portions of light from the beamsplitter. The second optical group is constructed to focus the first portion as a first image onto a first area of a common image sensor and the focus second portion as a second image onto a second area the common image sensor.

According to some implementations of the third aspect, the optical device is a camera head including a connector adapted to attach to and detach from an endoscope. The optical device may be a videoendoscope including a scope shaft connected to a camera head containing the first and second optical groups and the common image sensor.

According to some implementations of the third aspect, the first optical group may include a spectral filter whereby the spectral content of the first portion of light differs substantially from the spectral content of the second portion of light. The first portion of light may include infrared content, with the second portion of light including visible light.

According to some implementations of the third aspect, the first optical group may include a means to manipulate the light intensity of the first portion of light such that it has a different intensity than the second portion of light. The device may be connected to an image processor programmed to process the first and second images to generate a single combined image with higher dynamic range than either the first or second image taken individually.

According to some implementations of the third aspect, the device may include a focusing optical element in the first optical path that is not present in the second optical path such that the first image is brought to a different focus on the common image sensor. The device may be connected to an image processor programmed to process the first and second image to generate a single image with an enhanced depth of field over either the first or second image taken individually.

According to some implementations of the third aspect, the device may include a magnification means to manipulate the first portion of light such that the first and second image have a different magnification at the image sensor.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video. Directions such as upstream and downstream refer to the direction of light travel.

Because digital cameras, image sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 1:
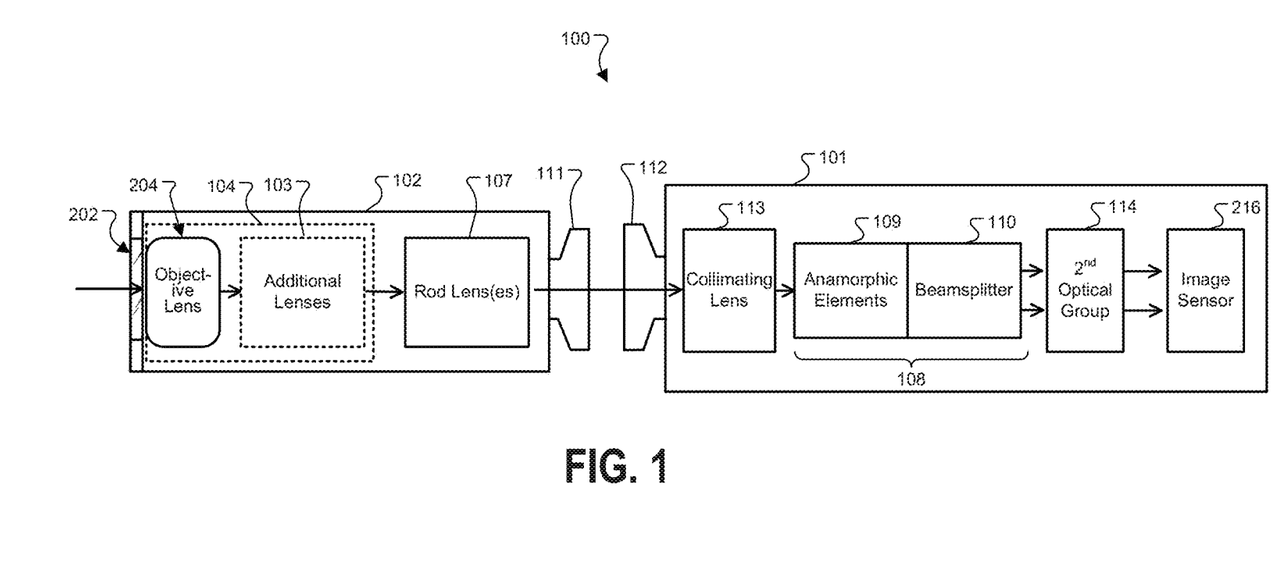
FIG. 1 is a block diagram of a medical imaging device 100 according to an example embodiment of the invention.

FIG. 1 is a block diagram of a medical imaging device 100 according to an example embodiment of the invention. Medical imaging device 100 ("device 100") includes a camera head 101 which may have an endoscope 102 attached via connectors 111 and 112. In some embodiments, an endoscope 102 and camera head 101 may be integrated into a single housing with no connectors needed. In some embodiments, the device 100 is provided as only the camera head 101 adapted to be connected to a suitable endoscope. Connectors 111 and 112 in this embodiment are standard eyecup style optical connectors but may be any suitable connector allowing light to pass from endoscope 102 to camera head 101. Various structural components supporting the depicted elements are omitted in the diagrams herein, as well as other components such as illumination lights sources and controls, which are known in the art and are not shown in order to avoid obscuring the relevant details of the example embodiments of the invention.

Camera head 101 includes a collimating lens or lens group 113 positioned at or behind a central window of connector 112 to receive and condition optical image light from the endoscope 102. Positioned in the optical channel after collimating lens 113 is a first substantially afocal optical group 108 that may include one or more anamorphic optical elements 109 optically arranged to receive the optical image light and alter the image light to have an anamorphic aspect ratio. It is noted that the beamsplitting techniques herein may be used with or without the anamorphic elements in various embodiments. Further, other manipulating optical means, such as a spectral filter or polarized filter, may be employed in place of or in addition to the anamorphic optical elements 109. In addition, these manipulating optical means may also be elements of the beamsplitter 110. Other versions may include another type of manipulating optical means such as, for example, a magnification means such as a magnifying lens to manipulate the first portion of light such that the first and second image have a different magnification at the image sensor. By the term "substantially afocal optical group," it is meant that collimating lens group 113 ensures that light passing through optical group 108 is substantially afocal, and, optical group 108 is not positioned in the image space of the optical system. A beamsplitter 110 is optically arranged to receive the optical image light in a substantially afocal state from the endoscope 102, passing through collimating lens 103, and split the optical image light into a first portion of light directed to a first optical path and a second portion of light directed to a second optical path as depicted by the two arrows showing the light path to common second optical group 114. The first and second optical paths are further described with respect to the example embodiments below. The splitting of afocal light ahead of the second, focusing, lens group 114, rather than in the image space after the light is focused, has the advantage of allowing a common back end to be used with various optical groups 108 having disparate functions, simplifying the optical design, development, and construction of the camera head. The use of a common image sensor allows efficient use of high resolution sensors, which provide enough pixel resolution to capture a plurality of images with sufficient resolution for many endoscope applications. Enhanced depth of field, high dynamic range (HDR), fluorescence imaging (FI) analysis (including indocyanine green (ICG) analysis), and polarization studies can benefit from the collection of varying versions of the same image. A further advantage is that the device may be used with a basic endoscope head allowing the pairing of stock endoscopes with a plurality of possible inventive imaging devices utilizing different front end components 108 for a variety of different applications.

The second optical group 114 is generally for focusing the substantially afocal light received from the first optical group 108 onto the image sensor. Second optical group 114 includes refractive elements optically arranged to receive the first and second portions of light from the beamsplitter 110 and focus the first portion as a first image onto a first area of a common image sensor 216 and the focus second portion as a second image onto a second area the common image sensor 216, different from the first area. The second optical group 114 typically includes at least one focusing lens, with the group having a total positive power. Many suitable lenses and combinations of lenses may be used for second optical group 114. The sensor signal, containing two images, is generally processed as further described with respect to FIG. 6 and FIG. 8 to provide a combined image.

In some embodiments, system 100 includes an endoscope 102 as depicted at the left of the block diagram. The depicted endoscope is an example only, and many endoscope and borescope designs are suitable, including rigid and flexible endoscopes and borescopes. Typically the endoscope will have an ocular (not shown) proximal to the rod lenses 107. The exemplar endoscope 102 includes a cover glass 202 at its distal tip, which in this version faces directly along the longitudinal axis of the endoscope 102, but may also be positioned at an angle relative to the longitudinal axis as is known in the art. Behind, or on the proximal side of, the cover glass 202 is shown a preferred position for the objective lens 204, set against or very near cover glass 202 and preferably assembled together with the cover glass in construction. While a wide-angle lens is preferred for objective lens 204, this is not limiting and any suitable lens may be used in various embodiments. Objective lens 204 may be part of an objective lens group 104 which may include one or more additional lenses 103. The particular number and arrangement of lenses in the endoscope 102 will vary widely depending on the application. Optically arranged or attached at the proximal side of objective lens 204 or objective lens group 104 is a series of one or more rod lenses 107 that serve to pass the light down endoscope 102 towards its proximal end. Typically several rod lenses 107 are employed, which may be separated by spacers or other lenses in any suitable manner known in the art. Also, while the endoscope 102 is typically rigid, known shaft design variations allow rod lenses to be used in a semi-flexible shaft in which flexible joints are present at one or more places along the shaft between the rod lenses while the shaft is rigid along the portions containing a rod lens. Such a shaft design may be used in various embodiments of the invention.

Figure 2:
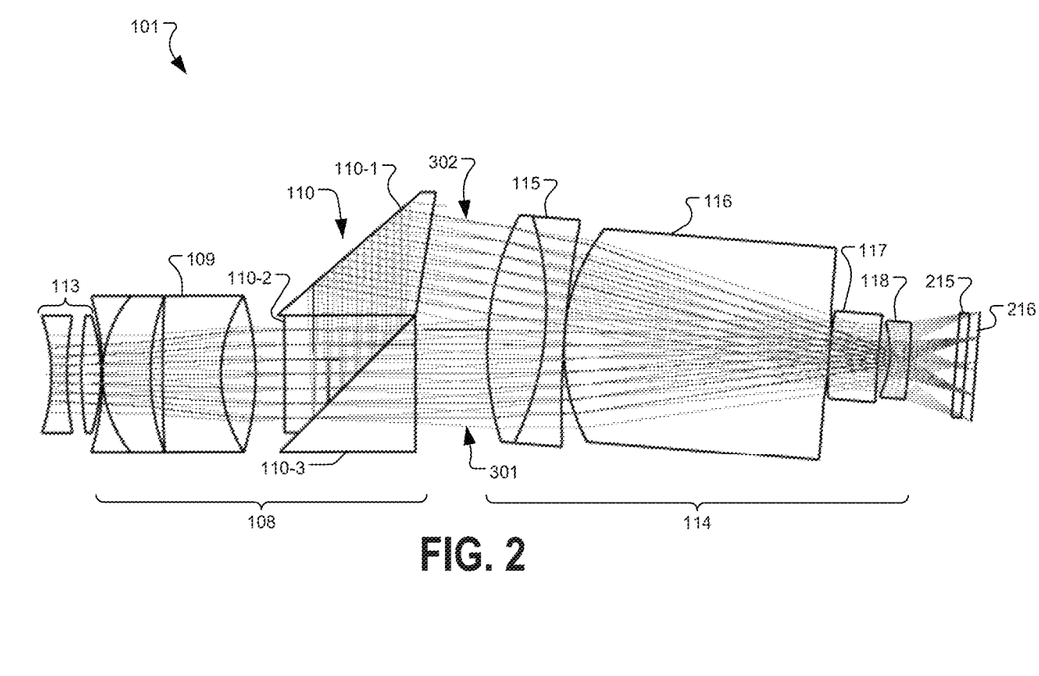
FIG. 2 is a partial cross section diagram of a camera head 101 showing the optical assembly construction according to an example embodiment.

FIG. 2 is a partial cross section diagram of a camera head 101 showing the optical assembly construction according to an example embodiment. The cross section includes a light ray diagram showing the passage of image light through the assembly to image sensor 216. The depicted optical elements are in diagram form only and are not drawn to scale. The depicted optical assembly may be employed with endoscope devices and systems having an integrated camera or an external detachable camera head. As shown, the optical assembly starts at collimating lens 113 where the image light enters the camera head. Collimating lens 113 may have a slightly positive or negative power in order to adjust the image light to the desired condition to be received by first optical group 108, preferably with light rays close to parallel. The collimating lens group 113 generally comprises a group of at least two elements, including a biconcave element followed by a bi-convex element, the two elements being adjustable with respect to each other to ensure that light exiting the collimating lens 113 is substantially afocal. First optical group 108 in this version includes one or more anamorphic optical elements 109 optically arranged to receive the optical image light and alter the image light to have an anamorphic aspect ratio. While anamorphic optical elements 109 are cylindrical lens elements in this version, any suitable anamorphic lens or combination of lenses may be used. Further, the anamorphic optical elements 109 may be constructed with any suitable optical elements for producing an anamorphic effect, such as shaped mirrors, for example.

A beamsplitter 110 is optically arranged to receive the optical image light in an afocal state and split the optical image light into a first portion of light directed to a first optical path 301 and a second portion of light directed to a second optical path 302. In this embodiment, beamsplitter 110 is constructed of prisms, including the two lower right angle prisms 110-2 and 110-3 with a suitable partially reflective coating along their adjacent surface, by which the image light is split with a first portion passing straight through along first optical path 301 and a second portion reflected upward along second optical path 302 as depicted. As discussed above, the first and second portions of light may comprise different spectral content, for example, as a result of the interface of prisms 110-3 and 110-2 comprising a dichroic filter, or, alternately by placing a color absorbing filter along optical paths 301 and/or 302. The second portion of light reflects off the reflective inner surface of the upper prism 110-1, which as shown has an angle greater than a right angle prism, approximately 105°, to direct the second optical path toward the second optical group 114.

Figure 7A:
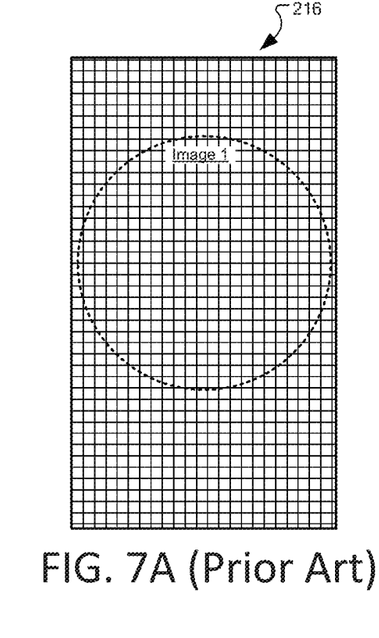
FIGS. 7A-7D are a series of diagrams showing examples of sensor area usage with various image projection designs.
Figure 7B:
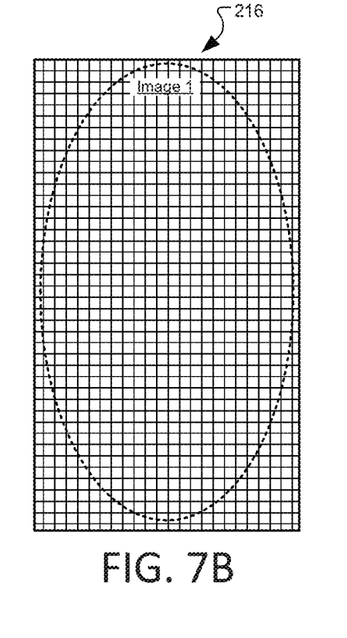
Figure 7C:
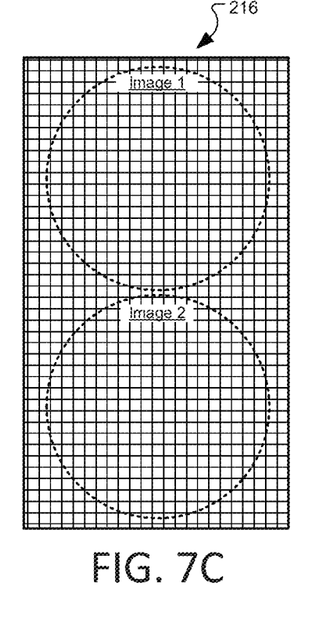
Figure 7D:
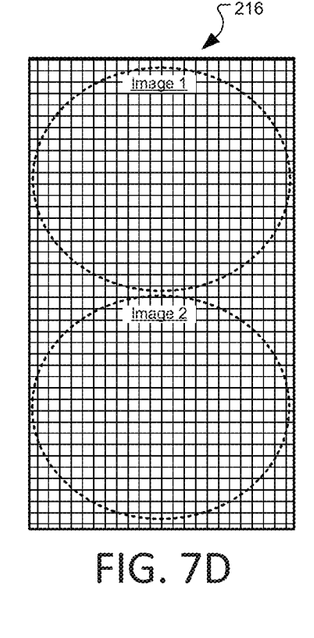

The second optical group 114 includes refractive elements optically arranged in both the first and second optical paths to receive the first and second portions of light from the beamsplitter 110 and focus the first portion as a first image onto a first area of a common image sensor 216 and the focus second portion as a second image onto a second area the common image sensor 216, different from the first area. Second optical group 114 typically includes at least one focusing lens, with the group having a total positive power. Many suitable lenses and combinations of lenses may be used for second optical group 114, with some additional examples shown in FIGS. 3-5. In this embodiment, second optical group 114 includes a doublet achromat lens 115 having a positive optical power, including a biconvex lens and concave-plano lens. As can be understood from the ray diagram, lens 115 and the rest of second optical group 114 are preferably symmetrically arranged with respect to the first and second optical paths 301 and 302, and large enough to span both paths. That is, second optical group 114 is positioned with the axis pointing between the first and second paths such that each path has similar incidence on lens 115, symmetrical about the central axis of group 114. As depicted, that is achieved by positioning second optical group 114 with its central axis at an angle that bifurcates the angle between first and second optical paths 301 and 302. I.e., in the diagram, first optical path 301 is horizontal while second optical path 302 is at a downward angle of approximately 15° as it exits the upper prism 110-1 of beamsplitter 110 because prism 110-1 is not at a right angle, making paths 301 and 302 converge. To provide a symmetrical effect on the light of both paths 301 and 302, the optical axis of second optical group 114 bifurcates the converging paths, in this example the second optical group 114 having its distal end tilted upward in the diagram at an angle of 7.5°, thereby providing similar processing to both the first and second portions of light. All the optical elements in the second group 114 are so tilted, and the sensor 216 and cover glass 215 are similarly tilted. Optically arranged proximal to doublet achromat lens 115 is a convex-planar lens 116 which further focuses both portions of light toward the sensor. Optically arranged to receive both portions of light from lens 116 is a lens 117, which is a meniscus having positive optical power. Next, a smaller concave-convex lens 118 with a negative power directs both portions of light toward cover glass 215 and image sensor 216, spreading both portions of light create a pair of images of the desired size at image sensor 216. FIG. 7 contrasts the various image detection possibilities at the rectangular sensor 216. It is immediately evident that much of the active sensor area is not utilized with traditional single, circular image collection methods known in the art and shown in FIG. 7A. A much more effective use of the sensor area is achieved by manipulating the image to have an anamorphic aspect ratio, as shown in FIG. 7B. Dual image systems according to the present invention, as shown in FIG. 7C, utilize a large number of available pixels and enable all of the benefits discussed above associated with capturing two versions of the same scene. FIG. 7D shows a still more improved result by combining both the benefits of the anamorphic aspect ratio as well as the capturing of two images simultaneously, making, thereby maximal use of a single image sensor. It should also be noted that while the dual image embodiments shown in FIG. 7C and FIG. 7D show a vertical distribution of images on the sensor, there may be embodiments wherein the images are made to fall upon the sensor in a horizontal or even diagonal orientation. For example, the anamorphic image creating means could result in a pair of images with longer vertical axes, rather than longer horizontal axes as shown, and the resulting images would fall side-by-side on the sensor.

Referring again to FIG. 2, while in this embodiment beamsplitter 110 directs the first and second optical paths 301 and 302 at a converging angle to each other for ease of focusing both images, this is not limiting, and other versions may not require a converging angle between the paths. For example, in other embodiments the beamsplitter 110 may direct the paths at a converging angle and use a second optical assembly large enough to receive and focus the paths onto the image sensor. Further, while lenses 115, 116, 117, and 118 in this embodiment focus and direct both portions of light, other versions may include one or more lenses that perform focusing or diverging operations on only a single one of the optical paths. For example, lens 115 and/or 116 might be replaced with a separate focusing lens for each path.

Figure 3:
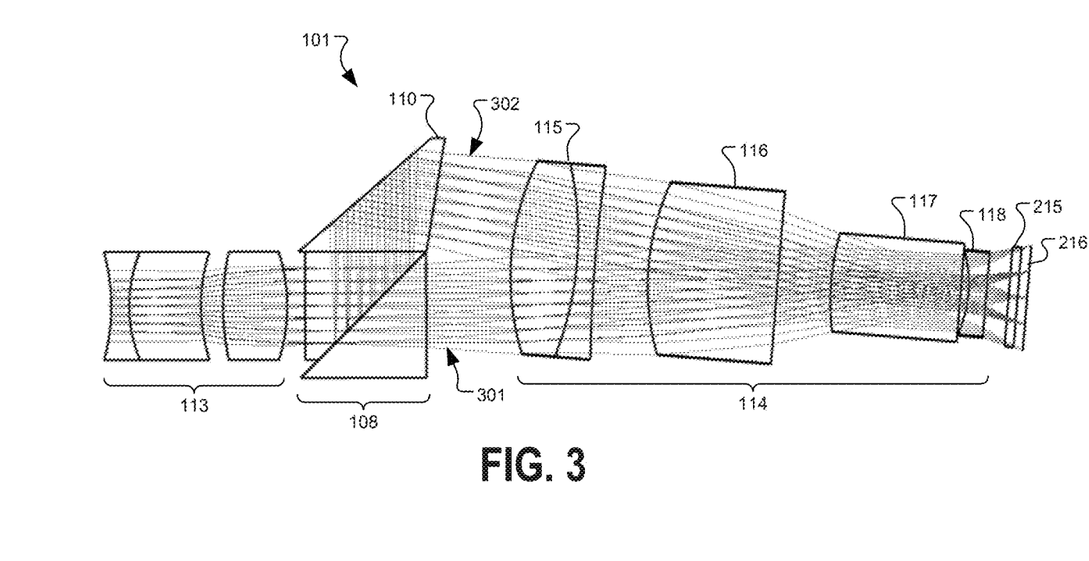
FIG. 3 is a cross section diagram of an optical assembly according to another embodiment.

FIG. 3 is a cross section diagram of an optical assembly according to another embodiment, also including a light ray diagram showing the passage of image light through the assembly to image sensor 216. The depicted optical elements are in diagram form only and are not drawn to scale. Like the other embodiments disclosed herein, this optical assembly may be employed with endoscope devices and systems having an integrated camera or an external detachable camera head. As shown, the optical assembly starts at collimating lens 113 where the image light enters the camera head. Collimating lens group 113 may have a slightly positive or negative power in order to adjust the image light to the desired condition to be received by first optical group 108. In this version, anamorphic elements are not used, and the collimating lens group 113 includes a convex-concave lens cemented to the proximal side of a meniscus lens with a negative optical power optically arranged to spread the image light to a desired size. Optically arranged in the proximal direction form these two elements is the third lens of the collimating lens group, a bi-convex lens, which has a positive optical power to collimate the image light. A beamsplitter 110 is optically arranged to receive the optical image light in an afocal state from the endoscope 102, via the collimating lens group, and split it into a first portion of light directed to a first optical path 301 and a second portion of light directed to a second optical path 302. In this embodiment, as in that shown in FIG. 2, beamsplitter 110 is constructed of prisms, and the first and second optical paths 301 and 302 are at a converging angle.

The second optical group 114 in this version also includes refractive elements optically arranged in both the first and second optical paths to receive the first and second portions of light from the beamsplitter 110 and focus the first portion as a first image onto a first area of a common image sensor 216 and the focus second portion as a second image onto a second area the common image sensor 216, different from the first area. Similarly to the previous embodiment, both optical paths are incident on a doublet achromat lens 115 having a positive optical power, including a biconvex lens and a concave-concave lens. Also like the previous embodiment, second optical group 114 is positioned with the axis pointing between the first and second paths such that each path has similar incidence on lens 115, symmetrical about the central axis of group 114. The optical elements in the second group 114 are tilted to provide this effect, and the sensor 216 and cover glass 215 are similarly tilted. In this embodiment, optical group 114 is relatively longer in comparison to first group 108, allowing the use of smaller elements with larger spacing. Optically arranged in the proximal direction to doublet achromat lens 115 is a concave-plano lens 116 which further focuses both portions of light toward the sensor.

Optically arranged to receive both portions of light from lens 116 is a lens 117, having positive optical power. Next, a smaller plano-concave lens 118 with a negative power directs both portions of light toward cover glass 215 and image sensor 216, spreading both portions of light create a pair of images of the desired size at image sensor 216.

Figure 4:
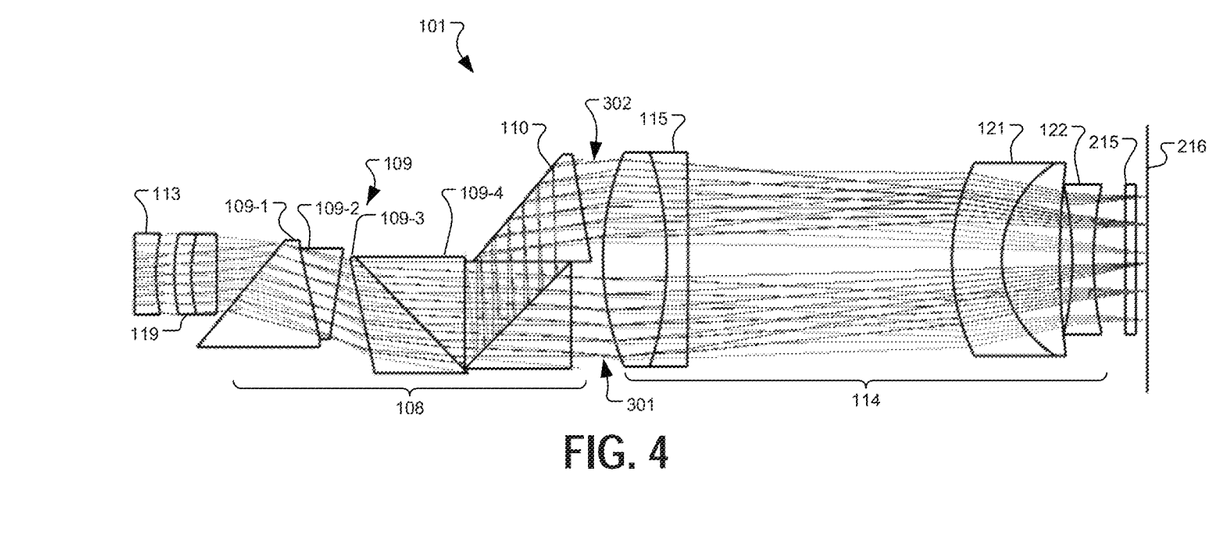
FIG. 4 is a partial cross section diagram of another example camera head optical assembly, using prisms for anamorphic elements.

FIG. 4 is a partial cross section diagram of an alternative embodiment of the inventive camera head optical assembly, using prisms as anamorphic elements. The cross section includes a light ray diagram showing the passage of image light through the assembly to image sensor 216. As shown, the optical assembly starts with a collimating and directing lens group 113, 119 where the image light enters the camera head. In this version the collimating and directing lens group includes a doublet lens 119 optically arranged to receive the image light from lens 113. Doublet lens 119 includes a convex-concave lens and a convex-plano lens. The overall collimating and directing lens group 113, 119 has a positive power for directing the image light in a substantially afocal state toward anamorphic optical elements 109 of first optical group 108. Optically arranged to receive the image light from lens 119 are anamorphic elements 109, which alter the image light to have an anamorphic aspect ratio. In contrast to the embodiment shown in FIG. 2, anamorphic optical elements 109 of this embodiment comprise four triangular prisms labeled 109-1 through 109-4. Prisms 109-1 and 109-2 together act as one prism of an anamorphic prism pair, paired with prism 109-3 and 109-4 acting as the other half of the anamorphic prism pair, to enlarge the vertical dimension of the image light while leaving the horizontal dimension (the direction into the page) unchanged. Each element of the pair is a doublet to make them achromatic. Other suitable combinations of prisms, including prism pairs, may be used to provide the desired anamorphic effect.

Beamsplitter 110 is optically arranged to receive the optical image light in an afocal state and split the optical image light into a first portion of light directed to a first optical path 301 and a second portion of light directed to a second optical path 302. In this embodiment, beamsplitter 110 is constructed of prisms, including the two lower right-angle prisms with a suitable partially reflective coating along their adjacent surface, by which the image light is split with a first portion passing straight through along first optical path 301 and a second portion reflected upward along second optical path 302 as depicted. As discussed above, the first and second portions of light may comprise different spectral content. The second portion of light reflects off the reflective inner surface of the upper prism, which in this version is a less-than right-angle prism, approximately 75° as can be seen on the drawing, to direct the second optical path toward the second optical group 114 with optical path 302 slightly diverging from optical path 301 as can be seen in the ray diagram.

The second optical group 114 includes refractive elements optically arranged in both the first and second optical paths 301 and 302 to receive the first and second portions of light from the beamsplitter 110 and focus the first portion as a first image onto a first area of a common image sensor 216 and the focus second portion as a second image onto a second area the common image sensor 216, different from the first area. In this embodiment, second optical group 114 includes a doublet achromat lens 115 having a positive optical power, including a biconvex lens and a concave-plano lens. As can be understood from the ray diagram, lens 115 and the rest of second optical group 114 are symmetrically arranged with respect to the first and second optical paths 301 and 302, and large enough to span both paths. That is, second optical group 114 is positioned with the axis pointing between the first and second paths such that each path has similar incidence on lens 115, symmetrical about the central axis of group 114. Similarly to the previous embodiment, this is done by positioning the optical axis of group 114 to bifurcate the angle between first and second optical paths 301 and 302, although in this embodiment group 114 is not tilted with respect to group 108. However in this case the optical paths are diverging. As can be seen on the ray diagram, the positive optical power of doublet lens 115 refracts both optical paths to converge toward doublet lens 121. The doublet lens 121 includes two adjacent convex-concave lenses which further focus both portions of light in the direction of sensor 216. Optically arranged to receive both portions of light from lens 121 is a biconcave lens 122, which has a negative power and serves to reduce the angle of incidence at which the focused image light hits sensor 216 behind cover glass 215. As with the version of FIG. 2, this version provides two anamorphic images formed on the same image sensor 216, which may include different characteristics either produced by the beamsplitter (such as spectrum, polarization, or intensity) or by additional lenses or filters in one of the first or second paths providing characteristics for one of the images that are not in the other. For example, an indocyanine green (ICG) imaging filter may be used, which only allows the wavelengths fluoresced by ICG dye (typically the near infrared region) to be passed in a selected one of the first or second optical paths. Such a filter may be included as part of the beamsplitter, with light split along the second optical path by reflective and dichroic surfaces or band-pass/band-reflect properties at the surfaces described. As with the other embodiments herein, the two images detected at sensor 216 are typically processed by the system camera control unit (CCU) to produce a final image based on both images. However for some applications the individual captured images may be displayed as may a combination of a single resultant image along with the generally unprocessed individual images.

Figure 5:
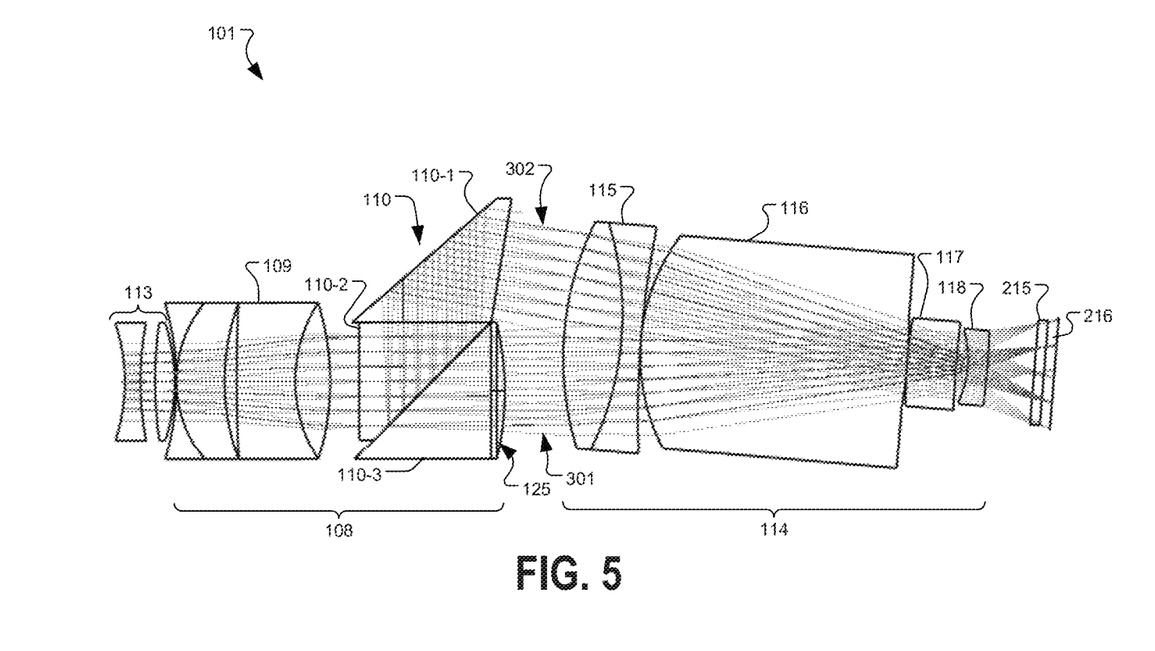
FIG. 5 is a partial cross section diagram of a camera head optical assembly similar to that of FIG. 2, but including an additional lens in the first optical path.

FIG. 5 is a partial cross section diagram of a camera head 101 optical assembly similar to that of FIG. 2, but including an additional lens in the first optical path. The cross section includes a light ray diagram showing the passage of image light through the assembly to image sensor 216. The anamorphic elements 109 of first optical group 108, the beamsplitter, and the lenses of second optical group 114 are similar to those of FIG. 2 and will not be described again. An additional plano-convex lens 125 with a positive optical power is included in this version, optically arranged in the first optical path 301 to receive the first portion of light from beamsplitter 110 and focus it, providing a modified focus to the image produced from the second portion of light in second path 302. This provides that the two images formed at sensor 216 each have a different focal depth and therefore include focal characteristics not present in the other image. The two images can be combined in processing to create an image with a larger depth of field. Various other optical elements or manipulating optical means may be placed in one or both of the optical paths such as at the location of lens 125 or optically arranged after prism 110-1 in the second optical path 302. For example, polarization filters, intensity filters, spectral filters, field stops, magnifying lenses, and other optical elements may be used. Further, one optical path length may be extended relative to the other by any appropriate means such as reflecting along a longer physical path or by including an optical element with a higher index of refraction in one path not provided in the other.

Figure 6:
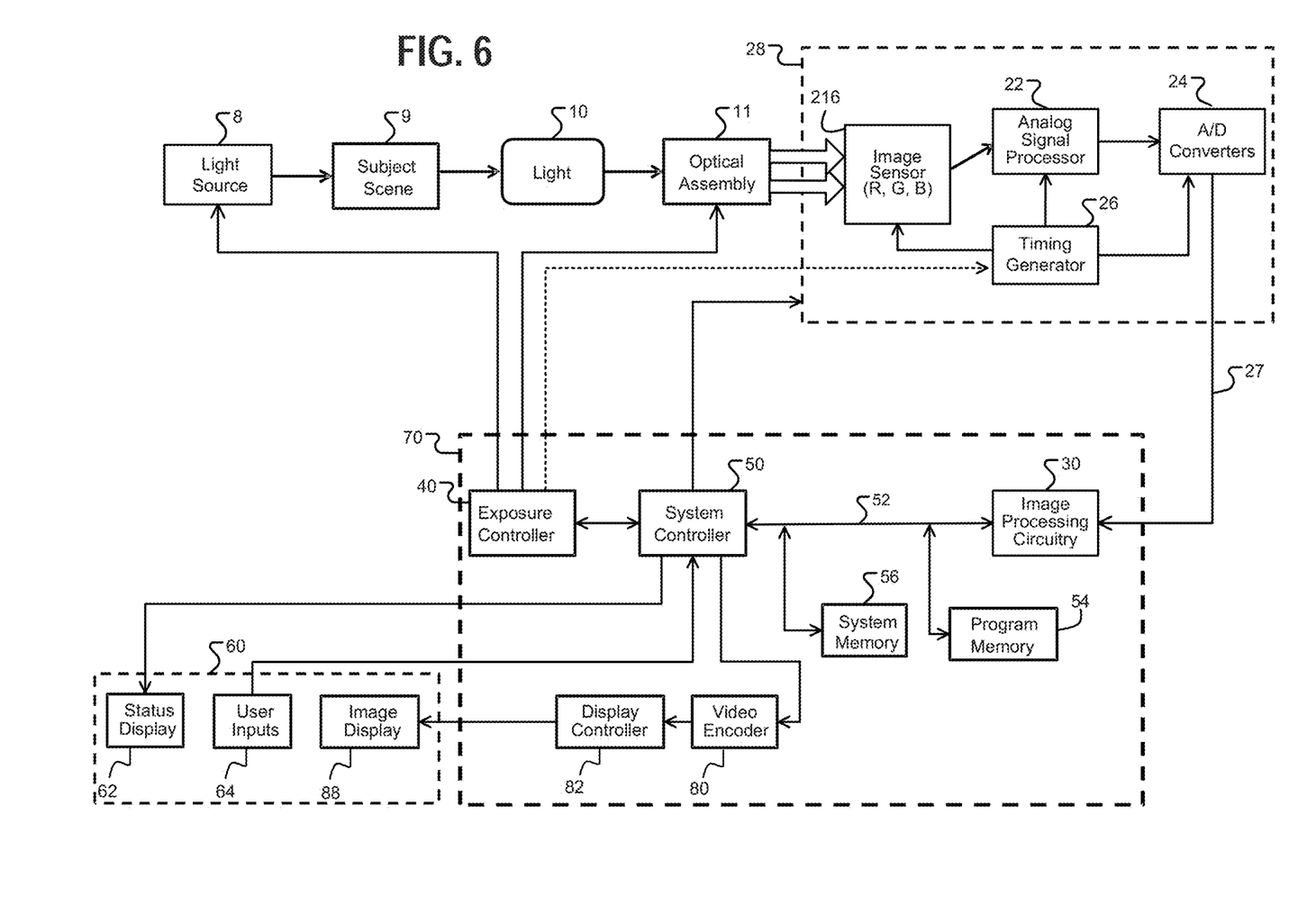
FIG. 6 is a hardware block diagram of system including an example image capture device according to an example embodiment of the invention.

FIG. 6 shows a block diagram of a system including an endoscope device and an image capture device having an improved dual image optical path as described above. The invention is applicable to more than one type of device enabled for image capture, such as Fl-capable endoscopes and other medical imaging devices. The preferred version is an imaging scope system, such as an endoscope.

As shown in the diagram of an endoscope device system, a light source 8 illuminates subject scene 9 with visible light. Fluorescent excitation light may also be used, which may be outside the visible spectrum, in the ultra-violet range or the infra-red/near infrared range, or both. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser diodes positioned at or near the front of the scope.

As shown in the drawing, light 10 reflected from (or, alternatively, as in the case of fluorescence, excitation light 8 absorbed and subsequently emitted by) the subject scene is input to an optical assembly 11, where the light is split as described herein and focused to form two images at a solid-state image sensor 216. Optical assembly 11 includes the optics of the endoscope and of the camera head. As discussed above, portions of the optical assembly may be embodied in a camera head or in a single imaging device. Image sensor 216 converts the incident light to an electrical signal by integrating charge for each picture element (pixel). The image sensor 216 may be constructed with any suitable sensor technology such as active pixel complementary metal oxide semiconductor sensor (CMOS APS) or a charge-coupled device (CCD), for example.

The total amount of light 10 reaching the image sensor 216 is regulated by the light source 8 intensity, the optical assembly 11 aperture, and the time for which the image sensor 216 integrates charge. An exposure controller 40 responds to the amount of light available in the scene given the intensity and spatial distribution of digitized signals corresponding to the intensity and spatial distribution of the light focused on image sensor 216. If fluorescence imaging is used, exposure controller 40 also controls the emission of fluorescent excitation light from light source 8, and may control the visible and fluorescent light emitting elements to be on at the same time, or to alternate to allow fluoresced light frames to be captured in the absence of visible light if such is required by the fluorescent imaging scheme employed. Exposure controller 40 may also control the optical assembly 11 aperture, and indirectly, the time for which the image sensor 216 integrate charge. The control connection from exposure controller 40 to timing generator 26 is shown as a dotted line because the control is typically indirect.

Timing generator 26 produces various clocking signals to select rows and pixels and synchronizes the operation of image sensor 216, analog signal processor 22, and A/D converter 24. Image sensor assembly 28 includes the image sensor 216, adjustment control, the analog signal processor 22, the A/D converter 24, and the timing generator 26. The functional elements of the image sensor assembly 28 can be fabricated as a single integrated circuit as is commonly done with CMOS image sensors or they can be separately-fabricated integrated circuits.

Analog signals from the image sensor 216 are processed by analog signal processor 22 and applied to analog-to-digital (A/D) converter 24 for digitizing the analog sensor signals. The digitized signals each representing streams of images or image representations based on the data are fed to image processor 30 as image signal 27. Typically both images will be transmitted together in signal 27 as a single image, which is separated in the image processing circuitry into dual image areas of the sensor (for example, image 1 and image 2, of FIG. 7C and FIG. 7D).

The system camera control unit (CCU) 70 includes image processing circuitry 30 performing digital image processing functions to process and filter the received images as is known in the art. Image processing circuitry may include separate, parallel pipelines for processing the first and second images separately. CCU 70 may be implemented in a single assembly or may include two or more camera control modules performing different functions such as communication with a specific camera model, and image processing. Such circuitry is known in the art and will not be further described here. Image processing circuitry 30 may provide algorithms, known in the art, for combining two images of the same view but containing different characteristics in a combined image display.

The system controller 50 controls the overall operation of the image capture device based on a software program stored in program memory 54. This memory can also be used to store user setting selections and other data to be preserved when the camera is turned off. System controller 50 controls the sequence of data capture by directing exposure controller 40 to set the light source 8 intensity, the optical assembly 11 aperture, and controlling various filters in optical assembly 11 and timing that may be necessary to obtain image streams. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays may be used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). In particular, the system controller 50 will typically have a mode toggle user input (typically through a button on the endoscope or camera head itself, but possibly through a GUI interface), and in response transmit commands to adjust image processing circuitry 30 based on predetermined setting stored in system memory. Preferably a system employed with any of the device designs herein provides ability to toggle between an individual view of either single image (for example, image 1 or image 2), both individual images, and/or a view of the combined image created with processing of data from both images. Settings may be provided to adjust the manner in which characteristics from the individual images are combined and displayed or stored. Settings may also include different settings for different models of scopes that may be attached to a camera head or other imaging device containing image sensor assembly 28.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80, and display controller 82 may be housed within CCU 70.

CCU 70 may be responsible for powering and controlling light source 8, image sensor assembly 28, and/or optical assembly 11. In some versions, a separate front end camera module may perform some of the image processing functions of image processing circuitry 30.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

Figure 8:
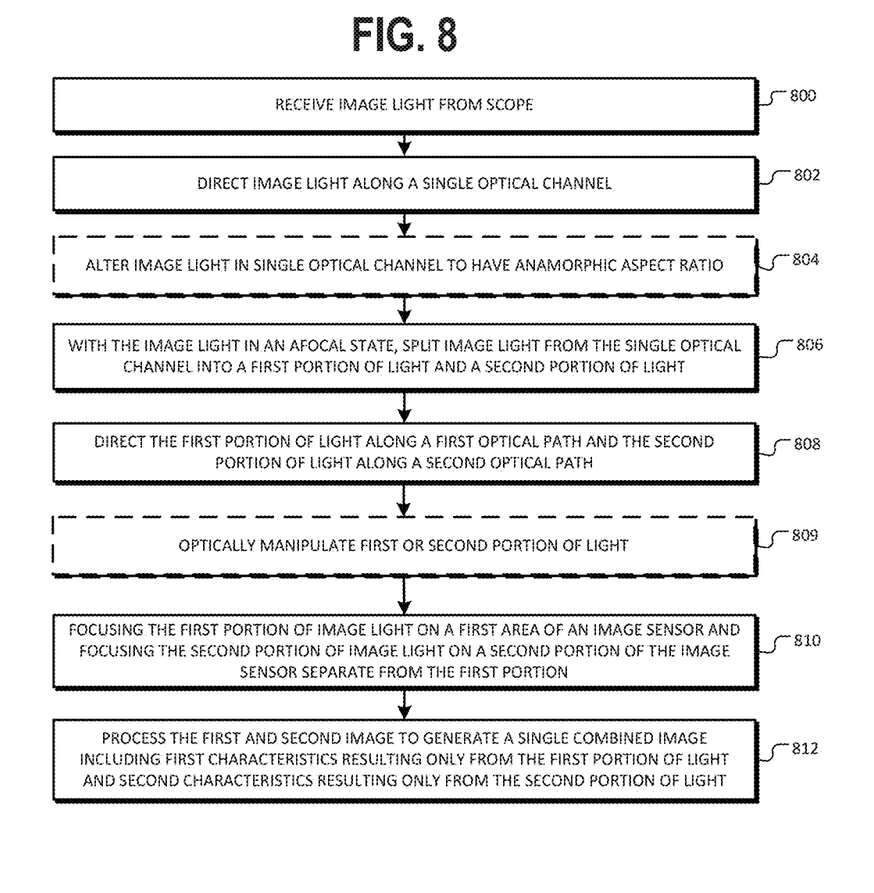
FIG. 8 is a flowchart of a method for producing endoscopy images according to an example embodiment.

FIG. 8 is a flowchart of a method for producing endoscopy images according to an example embodiment. The method may be performed employing any of the various example embodiments of a camera head or joint endoscope and camera head devices as described herein, with a suitable camera control unit such as that described above to process the image data. Other types of medical scopes or borescopes may be used in place of the endoscope as discussed above. The method begins at process block 800 where it includes receiving the image light from an endoscope. The endoscope device used may be a separate device attached to a camera head or an endoscope integrated with a camera head. At process block 802, the process directs the received image light along a single optical channel. At block 804, the process alters the image light, still in a single optical channel, to have an anamorphic aspect ratio. The final anamorphic ratio is selected to allow improved use of image sensor area when the image light is directed at the sensor. Some embodiments may not include block 804, or may instead optically manipulate the image light in another manner at this step. Next at process block 806, with the image light in an afocal state, the process includes splitting the image light from the single optical channel into a first portion of light and a second portion of light. Process block 806 may also operate to manipulate the first and second resulting beams relative to each other by selecting of the characteristics of the resulting beams that are allowed to pass directly through or be reflected by the beam splitting means. For example, beam splitting means at block 806 may include a dichroic beam splitter, resulting in the first portion of light to have different spectral content than the second portion of light. Then at block 808, the process directs the first portion of light along a first optical path and the second portion of light along a second optical path. Directing the light is preferably done with a beam splitter such as the example splitters described herein. Optionally, at block 809, the process may further optically manipulate the first and second portions of light relative to each other, for example by filtering, focusing, modifying the optical path length, or performing other optical manipulations to one or both of the portions of light. Next at process block 810 the process includes focusing the first portion of image light on a first area of an image sensor and focusing the second portion of image light on a second portion of the image sensor separate from the first portion. An example of the resulting areas is depicted in FIG. 7C and FIG. 7D, which show a example areas of rectangular image sensors 216, with the first portion of light hitting the sensor on the area shown as Image 1 and second portion of light hitting the sensor on the area shown as Image 2. As can be seen, the anamorphic aspect ratio makes greater use of the total sensor area than do the contrasting circular image areas on the sensor 216 shown in FIG. 7C. The anamorphic images are then corrected in image processing to yield the proper image aspect ratio.

Next at process block 812, image processing is performed on the image data from the sensor. The processing is generally applied to image data from both the first and second portions to generate a single combined image including first characteristics resulting only from the first portion of light and second characteristics resulting only from the second portion of light. The processing is performed by a CCU such as the CCU 70 of FIG. 6, or other suitable image processing circuitry.

The image characteristics from the different portions of light may be designed to be any of a number of characteristics desired to be measured through the endoscope. For example, in some versions the spectral content of the first portion of light differs substantially from the spectral content of the second portion of light. The first portion of light may include infrared content with the second portion of light including visible light, for example. A combined image based on such a scheme may use designated colors to show the infrared content superimposed on the visible light content in a manner known in the art. In another embodiment, the first portion of light has a different intensity range than the second portion. This may be accomplished by reflective characteristics of the beamsplitter, or by a filter or other suitable optical element placed in one of first or second optical paths. Processing the image data with different intensity ranges can be used to provide a high dynamic range (HDR) single combined image with higher dynamic range than either the first or second image taken individually. In another example embodiment, the process includes focusing the first image on the common image sensor differently than the focusing of the second image. The image processing of block 812 may extract features that are in sharper focus in one of the two images. Such an embodiment results in a single image with an enhanced depth of field over the first or second image taken individually. Still other embodiments may make use of a polarizing beamsplitter or with a polarizing filter in the first and/or second optical paths, allowing the dual images to each comprise light with a different polarization. Known image processing techniques for polarization studies may be applied in processing the dual images from such an embodiment, permitting, for example, glare reduction in the combined image.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An optical imaging system for use with a medical scope, comprising:
    a first optical group comprising a beamsplitter optically arranged to receive single optical image light in an afocal state and split the single optical image into a first portion of light directed along a first optical path and a second portion of light directed along a second optical path;
    a second optical group comprising refractive elements optically arranged to receive the first and second portions of light from the beamsplitter and focus the first portion as a first image onto a first area of a common image sensor and focus the second portion as a second image onto a second area the common image sensor wherein the first and second image areas of the common sensor do not overlap; and
    one or more manipulating optical means, comprising an anamorphic optical element in the first optical group, optically arranged to receive the single optical image light in an afocal state such that the resulting images have an anamorphic aspect ratio, located upstream of the second optical group to manipulate one or more of the single optical image light, the first portion of light and the second portion of light.

2. The optical imaging system according to claim 1 wherein one or more of the manipulating optical means comprises the beamsplitter, and wherein the beamsplitter manipulates the first portion of light such that it has different optical characteristics from the second portion of light.

3. The optical imaging system according to claim 1 wherein the anamorphic optical elements are prisms constructed to induce the anamorphic aspect ratio.

4. The optical imaging system according to claim 1 wherein the anamorphic optical elements are lenses constructed to induce the anamorphic aspect ratio.

5. The optical imaging system according to claim 1 wherein the one or more manipulating optical means further comprises a spectral filter whereby the spectral content of the first portion of light differs substantially from the spectral content of the second portion of light.

6. The optical imaging system according to claim 5 further comprising an image processor programmed to process the first and second images, and generating there from a single image wherein the different spectral content of the first and second images are overlaid.

7. The optical imaging system according to claim 5 wherein the first portion of light comprises infrared content and the second portion of light comprises visible light.

8. The optical imaging system according to claim 7 further comprising an image processor programmed to process the first and second images and generating there from a single image with the infrared content and visible light content.

9. The optical imaging system according to claim 1 wherein the one or more manipulating optical means comprises a means to manipulate the light intensity of the first portion of light such that it has a different intensity than the second portion of light.

10. The optical imaging system according to claim 9 further comprising an image processor programmed to process the first and second images to generate a single combined image with higher dynamic range than either the first or second image taken individually.

11. The optical imaging system according to claim 1 wherein the one or more manipulating optical means comprises an optical element in the first optical path that is not present in the second optical path such that the first image is brought to a different focus than the second image on the common image sensor.

12. The optical imaging system according to claim 11 further comprising an image processor programmed to process the first and second images to generate a single image with an enhanced depth of field over either the first or second image taken individually.

13. The optical imaging system according to claim 1 wherein the one or more manipulating optical means further comprises a magnification means to manipulate the first portion of light such that the first and second images have a different magnification at the image sensor.

14. The optical imaging system according to claim 13 further comprising an image processor programmed to process the first and second images and generate there from a single image comprising a magnified region with enhanced resolution and a non-magnified region, wherein the resulting single image has an enhanced resolution and field-of-view, over either image taken individually.

15. A method of producing enhanced images from a medical scope, comprising the steps of:
  collecting image light from an illuminated scene;
  directing image light from the medical scope along a single optical channel with the image light in a substantially afocal state;
  splitting the image light from the single optical channel into a first portion of light and a second portion of light;
  optically manipulating the image light directed along a single optical channel to have an anamorphic aspect ratio, the first portion of light, or the second portion of light;
  directing the first portion of light along a first optical path and the second portion of light along a second optical path;
  focusing the first portion of light on a first area of an image sensor and forming thereby a first detected image;
  focusing the second portion of light on a second portion of the image sensor, separate from the first area of the image sensor, and forming thereby a second detected image; and
  processing image data from the first and second portions of the image sensor.

16. The method of claim 15 comprising the further step of generating a single combined image by combining elements of the first detected image and elements of the second detected image.

17. The method of claim 15 wherein the step of optically manipulating one or more portions of light further comprises the step of filtering the spectral content such that the first portion of light differs substantially from the spectral content of the second portion of light.

18. The method of claim 17 wherein the step of filtering the spectral content comprises filtering wavelengths outside of the infrared spectrum such that the content of the first portion of light comprises infrared light and the second portion of light comprises visible light.

19. The method of claim 18 wherein the step of processing data comprises generating a single image with the infrared content and visible light content overlaid.

20. The method of claim 17 wherein the step of processing data comprises generating a single image with the different spectral content of the first and second images overlaid.

21. The method of claim 15 wherein the step of optically manipulating one or more portions of light further comprises the step of attenuating the first portion of light such that it has a different intensity than the second portion of light.

22. The method of claim 21 wherein the step of processing the image data comprises generating a single combined image with higher dynamic range than either the first or second detected image taken individually.

23. The method of claim 15 wherein step of optically manipulating one or more portions of light comprises the further step of focusing the first image on the common image sensor differently than focusing the second image on the common image sensor, and wherein the image processing step comprises generating a single image with an enhanced depth of field over that of either the first or second detected images taken individually.

24. An optical imaging system for use with a medical scope, comprising:
  a first optical group comprising a beamsplitter optically arranged to receive single optical image light in an afocal state and split the single optical image into a first portion of light directed along a first optical path and a second portion of light directed along a second optical path;
  a second optical group comprising refractive elements optically arranged to receive the first and second portions of light from the beamsplitter and focus the first portion as a first image onto a first area of a common image sensor and focus the second portion as a second image onto a second area the common image sensor wherein the first and second image areas of the common sensor do not overlap; and
  one or more manipulating optical means located upstream of the second optical group to manipulate the first portion of light relative to the second portion of light, at least one of the manipulating optical means selected from the group consisting of
  an optical element that causes the first image to be brought to a different focus than the second image on the common image sensor, or
  a magnification means to manipulate the first portion of light such that the first and second images have different magnification at the common image sensor.

25. The optical imaging system according to claim 24 wherein the one or more manipulating optical means comprises an optical element causing the first image to be brought to a different focus than the second image on the common image sensor, and further comprising an image processor programmed to process the first and second images to generate a single image with enhanced depth of field over either the first or second image taken individually.

26. The optical imaging system according to claim 24 wherein the one or more manipulating optical means comprises a magnification means, and further comprising an image processor programmed to process the first and second images to generate there from a single image comprising a magnified region with enhanced resolution and a non-magnified region, wherein the resulting single image has an enhanced resolution and field-of-view, over either image taken individually.

* * * * *